US00PP15707P2

(12) United States Plant Patent
Sakazaki

(10) Patent No.: US PP15,707 P2
(45) Date of Patent: Mar. 29, 2005

(54) ***CALIBRACHOA* PLANT NAMED 'USCALI48'**

(50) Latin Name: ***Calibrachoa* sp.**
Varietal Denomination: USCALI48

(75) Inventor: Ushio Sakazaki, Shiga (JP)

(73) Assignee: Plant 21 LLC, San Marco, CA (US)

( * ) Notice: Subject to any disclaimer, the term of this patent is extended or adjusted under 35 U.S.C. 154(b) by 0 days.

(21) Appl. No.: 10/827,541

(22) Filed: Apr. 19, 2004

(51) Int. Cl.[7] ..... A01H 5/00
(52) U.S. Cl. ..... Plt./263
(58) Field of Search ..... Plt./263

(56) References Cited

U.S. PATENT DOCUMENTS

PP10,278 P * 3/1998 Murakami ..... Plt./356

OTHER PUBLICATIONS

UPOV ROM GTITM Computer Database, GTI Jouve Retrieval Software 2004/04 Citations for 'USCALI48'.* http://www.rhs.org.uk/seedlist/documents/calibrachoa2003.pdf.* http://www.provenwinners–europe.com/pw/Eng/varieties30.htm.*

* cited by examiner

*Primary Examiner*—Kent Bell
*Assistant Examiner*—W C Haas
(74) *Attorney, Agent, or Firm*—C. A. Whealy

(57) ABSTRACT

A new and distinct cultivar of *Calibrachoa* plant named 'USCALI48', characterized by its semi-upright plant habit; freely branching habit; freely flowering habit; large white and purple bi-colored flowers; good weather tolerance; and resistance to *Thielaviopsis*.

1 Drawing Sheet

Botanical classification/cultivar designation: *Calibrachoa* sp. cultivar USCALI48.

CROSS REFERENCE TO RELATED APPLICATIONS

The present application is co-pending with the following related applications: *Calibrachoa* Plant Named 'USCALI4' (U.S. Plant patent application Ser. No. 10/827,545) and *Calibrachoa* Plant Named 'USCALI17' (U.S. Plant patent application Ser. No. 10/827,546).

BACKGROUND OF THE INVENTION

The present Invention relates to a new and distinct cultivar of *Calibrachoa* plant, botanically known as *Calibrachoa* sp., and hereinafter referred to by the cultivar name 'USCALI48'.

The new *Calibrachoa* is a product of a planned breeding program conducted by the Inventor in Hikone, Shiga, Japan. The objective of the program is to create new heat-tolerant and disease-resistant *Calibrachoa* cultivars with desirable plant habit and attractive flower colors.

The new *Calibrachoa* originated from a cross-pollination made by the Inventor on May 10, 1998 of a proprietary seedling selection of *Calibrachoa* identified as code number CJ14-2, not patented, as the female, or seed, parent with a proprietary seedling selection of *Calibrachoa* identified as code number CJ12-1, not patented, as the male, or pollen, parent. The new *Calibrachoa* was selected by the Inventor on Jun. 15, 1999 in a controlled environment in Gensingen, Germany.

Asexual reproduction of the new cultivar by terminal cuttings taken in a controlled environment in Gensingen, Germany since Jun. 25, 1999, has shown that the unique features of this new *Calibrachoa* are stable and reproduced true to type in successive generations.

SUMMARY OF THE INVENTION

Plants of the cultivar USCALI48 have not been observed under all possible environmental conditions. The phenotype may vary somewhat with variations in environment such as temperature, light intensity, daylength, water status and fertility level without, however, any variance in genotype.

The following traits have been repeatedly observed and are determined to be the unique characteristics of 'USCALI48'. These characteristics in combination distinguish 'USCALI48' as a new and distinct cultivar of *Calibrachoa:*

1. Semi-upright to eventually cascading plant habit.
2. Freely branching habit.
3. Freely flowering habit.
4. Large white and purple bi-colored flowers.
5. Good weather tolerance; tolerant to rain and low and high temperatures.
6. Resistant to *Thielaviopsis.*

Plants of the new *Calibrachoa* differ primarily from plants of the parent selections in plant habit as plants of the female selection are more upright than plants of the new *Calibrachoa* and plants of the male parent are more creeping than plants of the new *Calibrachoa.*

Plants of the new *Calibrachoa* can be compared to plants of the cultivar Million Bells Trailing White, U.S. Plant Pat. No. 10,278. In side-by-side comparisons conducted in Gensingen, Germany, plants of the new *Calibrachoa* had a more upright plant habit and larger flowers than plants of the cultivar Million Bells Trailing White.

Plants of the new *Calibrachoa* can also be compared to plants of the cultivar Colorburst White, not patented. In side-by-side comparisons conducted in Gensingen, Germany, plants of the new *Calibrachoa* had a more upright plant habit and larger flowers than plants of the cultivar Colorburst White.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new *Calibrachoa.*

The photograph at the top of the sheet comprises a side perspective view of a typical plant of 'USCALI48' grown in a container.

The photograph at the bottom of the sheet is a close-up view of typical flowers and leaves of 'USCALI48'.

DETAILED BOTANICAL DESCRIPTION

In the following description, color references are made to The Royal Horticultural Society Colour Chart, 1995 Edition, except where general terms of ordinary dictionary significance are used. Plants grown in 15-cm containers for about five weeks were used for the aforementioned photographs and following description. Plants were grown under conditions which closely approximate commercial production conditions during the summer in an outdoor nursery in Bonsall, Calif. During the production period, day temperatures ranged from 18 to 35° C. and night temperatures ranged from 7 to 18° C.

Botanical classification: *Calibrachoa* sp. cultivar USCALI48.

Parentage:

*Female, or seed, parent.*—Proprietary seedling selection of *Calibrachoa* sp. identified as code number CJ14-2, not patented.

*Male, or pollen, parent.*—Proprietary seedling selection of *Calibrachoa* sp. identified as code number CJ12-1, not patented.

Propagation:

*Type cutting.*—Terminal vegetative cuttings.

*Time to initiate and develop roots.*—Summer: About three weeks at 20° C. Winter: About four weeks at 20° C.

*Root description.*—Fine, freely-branching; whitish in color.

Plant description:

*Form/habit.*—Annual flowering plant; initially upright to semi-upright, eventually somewhat cascading; uniformly mounded appearance. Moderate growth rate; vigorous.

*Usage.*—Appropriate for hanging baskets, window boxes and patio containers.

*Plant height* (*from soil level to top of plant plane*).—About 14 cm.

*Plant diameter* (*area of spread*).—About 37 cm.

*Branching habit.*—Freely branching, about three primary branches per plant each with about eight to ten secondary lateral branches; pinching enhances lateral branch development.

*Lateral branch description.*—Length: About 20 cm. Diameter: About 2 mm. Internode length: About 9 mm. Texture: Coarse; pubescent. Color: 144A.

*Foliage description.*—Arrangement: Alternate until flowering, then opposite; simple. Length: About 2 cm. Width: About 5 mm. Shape: Oblanceolate. Apex: Broadly acute to rounded. Base: Attenuate. Margin: Entire. Texture, upper and lower surfaces: Slightly glandular; slightly pubescent. Venation pattern: Pinnate; arcuate. Color: Developing foliage, upper surface: 146A. Developing foliage, lower surface: 146B. Fully expanded foliage, upper surface: 147A. Fully expanded foliage, lower surface: 147B. Venation, upper surface: 147B. Venation, lower surface: 147C. Petiole: Length: About 5 mm. Diameter: About 1.5 mm. Color: 144B. Texture: Slightly pubescent.

Flower description:

*Flower type and habit.*—Flowers face upright or outwardly; single, axillary; salverform. Flowers persistent. Freely flowering habit, about 45 flower buds and open flowers per lateral stem. Flowers not fragrant.

*Natural flowering season.*—April to October in Southern California; flowering continuous during this period.

*Time to flower.*—Early flowering; plants begin flowering about four weeks after planting.

*Flower longevity on the plant.*—About one week.

*Flower size.*—Diameter: About 3 cm. Tube length: About 2.5 cm. Throat diameter: About 5 mm.

*Flower buds.*—Length: About 1.4 cm. Diameter: About 4 mm. Shape: Elongated oblong. Color: 155D.

*Corolla.*—Arrangement/appearance: Single whorl of five petals, fused into flared trumpet. Petal length from throat: About 1.2 cm. Petal width: About 1.7 cm. Petal shape: Roughly spatulate to obovate. Petal apex: Obtuse, rounded. Petal margin: Entire. Petal texture, upper and lower surfaces: Smooth, glabrous; velvety. Color: Petal, when opening, upper and lower surfaces: Close to 155D. Petal, opened flower, upper surface: Close to 155D; towards throat, 77C. Petal, opened flower, lower surface: Close to 155D. Flower throat (inside): 12B. Flower tube (outside): 2D.

*Sepals.*—Arrangement/appearance: Single whorl of five sepals, fused at base; star-shaped. Length: About 7 mm. Width: About 2 mm. Shape: Lanceolate. Apex: Acute. Margin: Entire. Texture, upper and lower surfaces: Smooth, glabrous. Color, upper and lower surfaces: 144A.

*Peduncles.*—Length: About 1.2 cm. Width: About 1 mm. Strength: Strong. Angle: About 45 to 60° from stem axis. Texture: Glabrous, smooth. Color: 145A.

*Reproductive organs.*—Stamens: Quantity: Five per flower. Anther shape: Rounded. Anther length: Less than 1 mm. Anther color: 12A. Pollen amount: Scarce. Pollen color: 12A. Pistils: Quantity: One per flower. Pistil length: About 8 mm. Stigma shape: Rounded. Stigma color: 145A. Style length: About 6 mm. Style color: 145D. Ovary color: 145B.

*Seed/fruit.*—Seed and fruit production has not been observed.

Disease/pest resistance: Plants of the new *Calibrachoa* have been noted to be resistant to *Thielaviopsis,* which causes black root rot or basal stem rot. Plants of the new *Calibrachoa* have not been noted to be resistant to other pathogens and pests common to *Calibrachoas.*

Weather/temperature tolerance: Plants of the new *Calibrachoa* are tolerant to rain and wind and have been observed to tolerate temperatures from −4 to 38° C.

It is claimed:

1. A new and distinct cultivar of *Calibrachoa* plant named 'USCALI48', as illustrated and described.

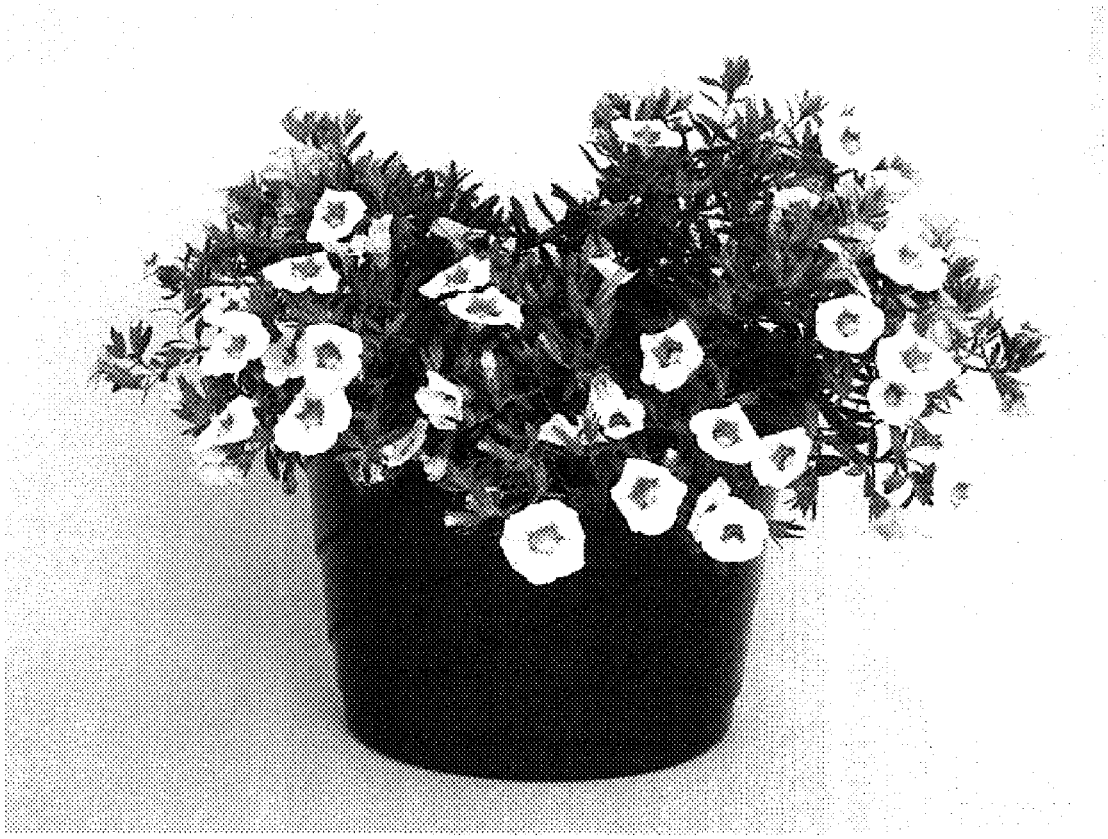
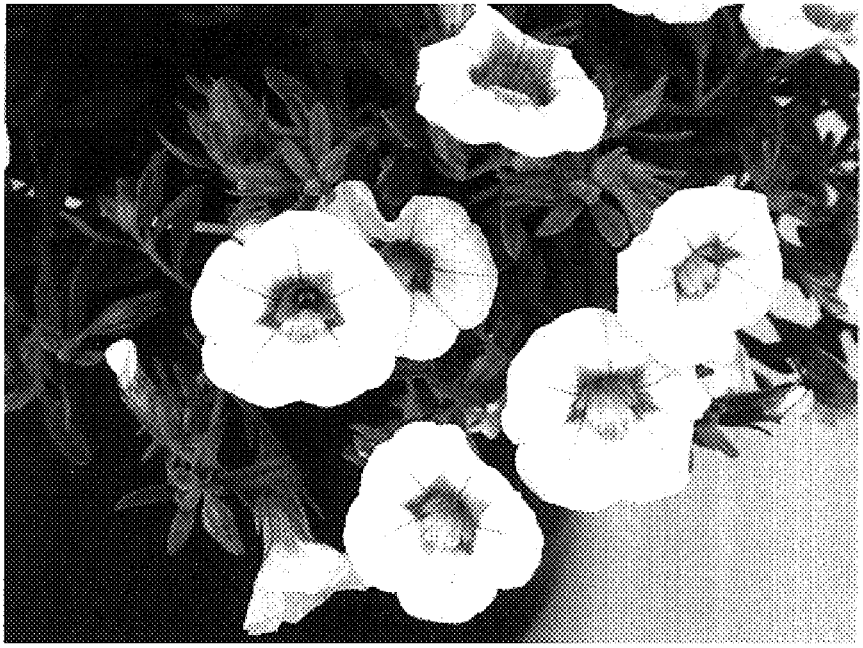

* * * * *